(12) United States Patent
Yamaguchi (10) Patent No.: US 9,672,330 B2
(45) Date of Patent: Jun. 6, 2017

(54) MASS SPECTROMETER (75) Inventor: Shinichi Yamaguchi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 1091 days.

(21) Appl. No.: 12/739,335

(22) PCT Filed: Oct. 23, 2007

(86) PCT No.: PCT/JP2007/001156
§ 371 (c)(1),
(2), (4) Date: Jul. 7, 2010

(87) PCT Pub. No.: WO2009/054026
PCT Pub. Date: Apr. 30, 2009

(65) Prior Publication Data
US 2010/0312489 A1 Dec. 9, 2010

(51) Int. Cl.
*G01N 33/48* (2006.01)
*G06F 19/00* (2011.01)
*G01N 33/68* (2006.01)
*H01J 49/00* (2006.01)
*G06G 7/58* (2006.01)

(52) U.S. Cl.
CPC ....... *G06F 19/703* (2013.01); *G01N 33/6848* (2013.01); *H01J 49/004* (2013.01); *H01J 49/0027* (2013.01)

(58) Field of Classification Search
CPC ............................ G01N 33/6848; G06F 19/16
See application file for complete search history.

(56) References Cited

U.S. PATENT DOCUMENTS

2007/0187588 A1  8/2007  Yoshinari et al.

FOREIGN PATENT DOCUMENTS

| EP | 2 208 990 | 7/2010 |
|---|---|---|
| JP | 08-124519 A | 5/1996 |
| JP | 10-142196 A | 5/1998 |
| JP | 10-293120 A | 11/1998 |
| JP | 11-064285 A | 3/1999 |
| JP | 2001-249114 A | 9/2001 |
| JP | 2007-218692 A | 8/2007 |

OTHER PUBLICATIONS

International Search Report of PCT/JP2007/001156 dated Jan. 15, 2008.
International Preliminary Report on Patentability (English Translation) dated Jun. 1, 2010.
S. Yamaguchi, et al., "Automated Detection of Metabolites from Liquid Chromatography/Mass Spectrometry/ Mass Spectrometry Data Using Partial Least Squares with Ion Trap Time of Flight Mass Spectrometry," J. Mass Spectrom. Soc. Jpn., 2007, pp. 83-89, vol. 55, No. 2.
G. Zurek, et al., "Novel Strategies for Metabolite Indetification Using HPLC-Ion Trap Mass Spectrometry," The Application Notebook, Jun. 2003, pp. 13-14.
Supplementary European Search Report dated Apr. 3, 2012, issued in corresponding European Patent Application No. 07827935.3.
Walter A Korfmacher et al: "HPLC-API/MS/MS: a powerful tool for integrating drug metabolism into the drug discovery process", Drug Discovery Today, vol. 2, No. 12, Dec. 12, 1997 (Dec. 12, 1997), pp. 532-537, XP55022914.
Mike S Lee et al: "Rapid Identification of Drug Metabolites with Tandem Mass Spectrometry", Biomedical and Environmental Mass Spectrometry, vol. 15, Jan. 1, 1988 (Jan. 1, 1988), pp. 193-204, XP55022743.
Ma Shuguang et al: "Application of Mass Spectrometry for Metabolite Identification", Current Drug Metabolism, Bentham Science Publishers, US, vol. 7, No. 3, Jul. 1, 2006 (Jul. 1, 2006), pp. 503-523, XP008150158, issn: 1389-2002, DOI: 10.2174/138920006777697891.
European Office Action issued May 13, 2015 in European Patent Application No. 07827935.3.
Beausoleil Sean A et al.: "Large-scale characterization of HeLa cell nuclear phosphoproteins", Proceedings of the National Academy of Sciences, National Academy of Sciences, US, vol. 101, No. 33, Aug. 17, 2004, pp. 12130-12135.
Steve M. M. Sweet et al: "Strategy for the Identification of Sites of Phosphorylation in Proteins: Neutral Loss Triggered Electron Capture Dissociation", Analytical Chemistry, vol. 78, No. 21, Nov. 1, 2006, pp. 7563-7569.
Gargi Choudhary et al.: "Application of a Data Dependent(TM) Neutral-Loss Experiment on the Finnigan LTQ(TM) for the Identification of Phosphorylated Peptides," Jan. 1, 2003, pp. 1-13.
Sheng Zhang et al.: "Data-Dependent TM Neutral-Loss Mass Spectrometry for the Identification of Protein Phosphorylation", Jan. 1, 2004, pp. 1-8.

*Primary Examiner* — Eric S Dejong
(74) *Attorney, Agent, or Firm* — Sughrue Mion, PLLC (57) ABSTRACT

A product ion spectrum is created on the basis of $MS^2$ analysis data respectively obtained for a parent compound and a metabolite (S1 and S2). Additionally, a neutral loss spectrum, in which the mass of each product ion is replaced with a mass difference between the mass of the product ion and that of a precursor ion, is created (S3). Then, a common peak having the same mass on the neutral loss spectrums of both the parent compound and the metabolite is extracted (S4), and a complementary peak appearing on the product ion spectrum of the metabolite is extracted (S5); this peak appears at a position corresponding to the difference between the mass of the common peak and that of the precursor ion. The ion corresponding to the complementary peak is designated as a precursor ion for the next $MS^3$ analysis (S6), and this $MS^3$ analysis is performed (S7). By a dissociation operation, if a portion common to the parent compound and the metabolite is desorbed in the form of a neutral molecule while a different portion remains in the form of an ion, an $MS^3$ analysis in which the ion of the different portion is used as the precursor ion is performed to obtain structural information of a site of metabolism.

2 Claims, 4 Drawing Sheets

(a) MS² SPECTRUM OF PARENT COMPOUND (A)

(b) MS² SPECTRUM OF METABOLITE (B)

(c) MS² MASS-DIFFERENCE SPECTRUM OF METABOLITE (B)

MASS SPECTROMETER

CROSS REFERENCE TO RELATED APPLICATIONS

This application is a National Stage of International Application No. PCT/JP2007/001156 filed Oct. 23, 2007, the contents of all of which are incorporated herein by reference in their entirety.

TECHNICAL FIELD

The present invention relates to a mass spectrometer capable of an $MS^n$ analysis where n is an integer greater than two.

BACKGROUND ART

In the field of mass analysis using an ion trap mass spectrometer or other apparatuses, a technique called the MS/MS analysis (or tandem analysis) is conventionally known. In a general MS/MS analysis, an ion having a specific mass (or mass-to-charge ratio, m/z, to be exact) is first selected as a precursor ion from an object to be analyzed. Next, the selected precursor ion is dissociated by a collision induced dissociation (CID) process to produce product ions (also called fragment ions). The resulting product ions are subjected to a mass analysis to obtain information relating to the mass of the product ions, the ions and neutral molecules desorbed by the dissociation operation, and other particles. Based on this information, the composition and chemical structure of the target sample molecule are deduced.

In recent years, samples to be analyzed with this type of system have been progressively increasing in molecular weight and becoming more complex in structure (composition). Therefore, depending on the nature of the sample, it is possible that the sample cannot be dissociated into sufficiently small masses by only one stage of the dissociation process. In such a case, an $MS^n$ analysis may be performed, where the dissociation operation is repeated two or more times and the eventually obtained product ions are subjected to mass analysis (for example, refer to Patent Document 1, 2 or other documents). The aforementioned MS/MS analysis is an $MS^n$ analysis where n=2.

By the way, analyzing metabolites resulting from chemical changes in a living organism has been a crucial subject in many fields, such as the diagnosis of various kinds of disease and illness, the assessment of the effectiveness and safety of drugs and functional foods, and the research on lifestyle and health. In recent years, a method called Metabolomics for exhaustively analyzing a metabolite has been attracting attention. In this metabolite analysis, when it is necessary to search for a compound resulting from a metabolism of another compound having a known structure (this compound will be hereinafter called a "parent compound", and the former compound will be called a "metabolite"), the aforementioned method using $MS^n$ spectrums collected by subjecting the parent compound having a large molecular weight to one or more stages of the dissociation operation is useful.

In the case of applying an $MS^n$ analysis to a metabolite analysis, it is necessary to perform a multi-stage dissociation operation on the site of metabolism specific to the metabolite (i.e. the portion modified by a part of the structure originating from the parent compound) in order to clarify the chemical structure of the metabolite. That is to say, it is important that an appropriate ion among a number of peaks of the product ions obtained by a given stage of the dissociation operation should be selected as the precursor ion for the next stage of the dissociation operation. In one conventional method for automatically selecting the precursor ion, a plurality of peaks with signal intensities equal to or greater than a predetermined threshold are extracted from the peaks appearing on a mass spectrum and subjected to a selection process using a specific criterion (e.g. in the order of decreasing intensities or increasing mass-to-charge ratios). However, this conventional precursor ion selection method does not guarantee that the ion corresponding to the site of metabolism in question will be always selected.

Therefore, in practice, an analysis operator visually checks the $MS^n$ spectrum to select an ion appropriate as the next precursor ion or specify the order of priority for selecting the precursor ion. However, making such decisions is rather difficult, and the correctness of the decision inevitably depends on the experience, skill and other factors of the analysis operator.

Patent Document 1: Japanese Unexamined Patent Application Publication No. H10-142196
Patent Document 2: Japanese Unexamined Patent Application Publication No. 2001-249114

DISCLOSURE OF THE INVENTION

Problem to be Solved by the Invention

The present invention has been developed to solve the aforementioned problems, and its objective is to provide a mass spectrometer capable of, when performing an analysis (e.g. the deduction of the chemical structure) of a plurality of components having similar chemical structures, as in the case of a parent compound and metabolite, using the MS spectrums, automatically selecting an appropriate precursor ion for the analysis or presenting information of the precursor ion to be analyzed with a higher priority.

Means for Solving the Problems

A first aspect of the present invention aimed at solving the aforementioned problem is a mass spectrometer capable of an $MS^n$ analysis (where n is an integer greater than two), which is characterized by including:

a) a mass spectrum creating means for creating an $MS^{m-1}$ spectrum (where m is an integer greater than two and no greater than n) based on mass analysis data obtained by an $MS^{m-1}$ analysis performed for each of the first and second components;

b) a mass-difference spectrum creating means for calculating, for each of the two $MS^{m-1}$ spectrums, a mass difference between the mass of each peak among some or all of the peaks appearing on the $MS^{m-1}$ spectrum and the mass of the precursor ion, and for creating an $MS^{m-1}$ mass-difference spectrum having a peak at each of the calculated mass differences;

c) a common-peak extracting means for extracting a peak having the same mass in the two $MS^{m-1}$ mass-difference spectrums relating to the first component and the second component;

d) a complementary-peak extracting means for extracting a complementary peak on the $MS^{m-1}$ spectrum relating to the first component and/or the second component, the complementary peak corresponding to a mass difference between the mass of the precursor ion and the mass of the common peak; and e) an analysis control means for conducting an $MS^m$ analysis so that the first component and/or the second component is subjected to the m−1-th stage of a dissociation operation with an ion corresponding to the complementary peak designated as the precursor ion.

A second aspect of the present invention aimed at solving the aforementioned problem is a mass spectrometer capable of an $MS^n$ analysis (where n is an integer greater than two), which is characterized by including:

a) a mass spectrum creating means for creating an $MS^{m-1}$ spectrum (where m is an integer greater than two and no greater than n) based on mass analysis data obtained by an $MS^{m-1}$ analysis performed for each of the first and second components;

b) a mass-difference spectrum creating means for calculating, for each of the two $MS^{m-1}$ spectrums, a mass difference between the mass of each peak among some or all of the peaks appearing on the $MS^{m-1}$ spectrum and the mass of the precursor ion, and for creating an $MS^{m-1}$ mass-difference spectrum having a peak at each of the calculated mass differences;

c) a common-peak extracting means for extracting a peak having the same mass in the two $MS^{m-1}$ mass-difference spectrums relating to the first component and the second component;

d) a complementary-peak extracting means for extracting a complementary peak on the $MS^{m-1}$ spectrum relating to the first component and/or the second component, the complementary peak corresponding to a mass difference between the mass of the precursor ion and the mass of the common peak; and e) an analysis control means for designating an ion corresponding to the complementary peak as a candidate of the precursor ion for the m−1-th stage of a dissociation operation in the process of performing an $MS^m$ analysis on the first component and/or the second component.

A third aspect of the present invention aimed at solving the aforementioned problem is a mass spectrometer capable of an $MS^n$ analysis (where n is an integer greater than two), which is characterized by including:

a) a mass spectrum creating means for creating an $MS^{m-1}$ spectrum (where m is an integer greater than two and no greater than n) based on mass analysis data obtained by an $MS^{m-1}$ analysis performed for each of the first and second components;

b) a common-peak extracting means for extracting a peak having the same mass in the two $MS^{m-1}$ spectrums relating to the first component and the second component; and c) an analysis control means for either excluding an ion corresponding to the common peak, or giving a low degree of priority to this ion, as a candidate of the precursor ion for the m−1-th stage of a dissociation operation to be performed in an $MS^m$ analysis on the first component and/or the second component.

An example of the mass spectrometer capable of an $MS^n$ analysis is an ion-trap mass spectrometer using an ion trap, which is typically a three-dimensional quadrupole ion trap. The dissociation of precursor ions is normally achieved by collision-induced dissociation. However, other methods may be used to dissociate precursor ions.

Any components may be chosen as the first component and the second component. However, applying the present invention to two components having totally different chemical structures will produce no significant results. Therefore, it is practically useful to choose two components having similar chemical structures. For example, given a certain compound as the first component, a metabolite produced from this compound by a metabolism in a living organism or other environments may be chosen as the second component.

The $MS^n$ spectrum created by the mass spectrum creating means is a mass spectrum reflecting the intensity of the product ions (or residual precursor ions that have not been dissociated) actually detected by a detector in the mass spectrometer. By contrast, the $MS^n$ mass-difference spectrum created by the mass-difference spectrum creating means changes its meaning depending on the valence of the precursor ion. If the precursor ion is monovalent, the $MS^n$ mass-difference spectrum reflects the intensity of neutral molecules that have been desorbed and excluded from the precursor ion by dissociation (neutral loss); therefore, this spectrum can be regarded as a virtual mass spectrum relating to some substances that have not been actually detected. If the precursor ion is multivalent, the $MS^n$ mass-difference spectrum reflects the intensity of the desorbed ions that have been actually detected.

For example, the complementary peak on the $MS^{m-1}$ spectrum relating to the first component is the peak that appears at a mass value of Mb−Ma, where Ma is the mass of a common peak on the $MS^{m-1}$ mass-difference spectrums relating to the first and second components and Mb is the mass of the precursor ion used in the $MS^{m-1}$ analysis of the first component (Mb>Ma). Similarly, the complementary peak on the $MS^{m-1}$ spectrum relating to the second component is the peak that appears at a mass value of Mc−Ma, where Ma is the mass of a common peak on the $MS^{m-1}$ mass-difference spectrums relating to the first and second components and Mc is the mass of the precursor ion used in the $MS^{m-1}$ analysis of the second component (Mc>Ma).

In the case where the first component and second component have similar chemical structures and a portion of their chemical structures has been disconnected in the form of fragments by a collision-induced dissociation or similar dissociation operation, if the fragments having a common chemical structure are neutral molecules, these fragments will appear as a common peak on the $MS^{m-1}$ mass-difference spectrums. Furthermore, even in the case where the fragments having a common chemical structure are ions, if the precursor ion is a multivalent ion, it is possible for those fragments to appear as a common peak on the $MS^{m-1}$ mass-difference spectrums. Conversely, it is possible to infer that an ion appearing as a complementary peak on the $MS^{m-1}$ spectrums is a portion that differentiates the first component from the second one in their chemical structure; this portion corresponds to the site of metabolism in the case where the first component is a parent compound and the second component is a metabolite. If the aforementioned ion is an ion corresponding to the site of metabolism, it is possible to choose this ion as a precursor ion for the next stage of the dissociation operation so as to further break down the structure of the site of metabolism and obtain useful information for estimating this structure.

Effect of the Invention

Accordingly, in the mass spectrometer according to the first aspect of the present invention, under the command of the analysis control means, an ion appearing as a complementary peak on the $MS^{m-1}$ spectrum in the previously described form is automatically designated as the precursor ion for the next stage of the dissociation operation, and an $MS^m$ analysis is performed using this precursor ion. The mass spectrometer according to the second aspect of the present invention does not immediately perform an $MS^m$ analysis using an automatically designated precursor ion; instead, it locates one or more ions appearing as complementary peaks on the $MS^{m-1}$ spectrum and lists them as candidates of the precursor ion for the dissociation operation in the next stage. The listed precursor ions can be ranked at higher priority levels in the case where a higher degree of priority should be given to an ion that is more likely to provide reliable information for the structural analysis or other purposes.

Thus, the mass spectrometers according to the first and second aspects of the present invention can collect mass analysis data of the first and second components having similar chemical structures while focusing on a portion having a different structure. Regarding the selection of a precursor ion corresponding to this portion, the analysis operator will be considerably released from the task of analyzing $MS^n$ spectrums to judge whether a given ion is appropriate for the precursor ion. Even an operator with insufficient experience or skills in this task can also collect appropriate information and efficiently conduct the structural analysis.

On the other hand, in the case where the first and second components have similar chemical structures and one or more portions of their chemical structures have been broken into fragments by a collision-induced dissociation or similar dissociation operation, if a fragment common to their chemical structures is an ion, the fragment will appear as a common peak on the $MS^{m-1}$ spectrums. In this case, an $MS^m$ analysis using the ion corresponding to this common peak as the precursor ion is less likely to provide information relating to the structure of the site of metabolism. Accordingly, in the mass spectrometer according to the third aspect of the present invention, an ion appearing as a common peak on the $MS^{m-1}$ spectrums is either excluded from the candidates of the precursor ion for the next stage of the dissociation operation or given a low priority to be designated as the precursor ion. This operation prevents unnecessary analyses that are not beneficial for the structural analysis, and consequently improves the efficiency of the structural analysis.

EXPLANATION OF NUMERALS

1 . . . Mass Analyzer Unit
2 . . . Ion Source
3 . . . Ion Optical System
4 . . . Ion Trap
5 . . . Time-of-Flight Mass Separator (TOF)
6 . . . Detector
10 . . . Central Controller
11 . . . Analysis Controller
12 . . . Data Processor
13 . . . Operation Unit
14 . . . Display Unit

BEST MODE FOR CARRYING OUT THE INVENTION

Figure 1:
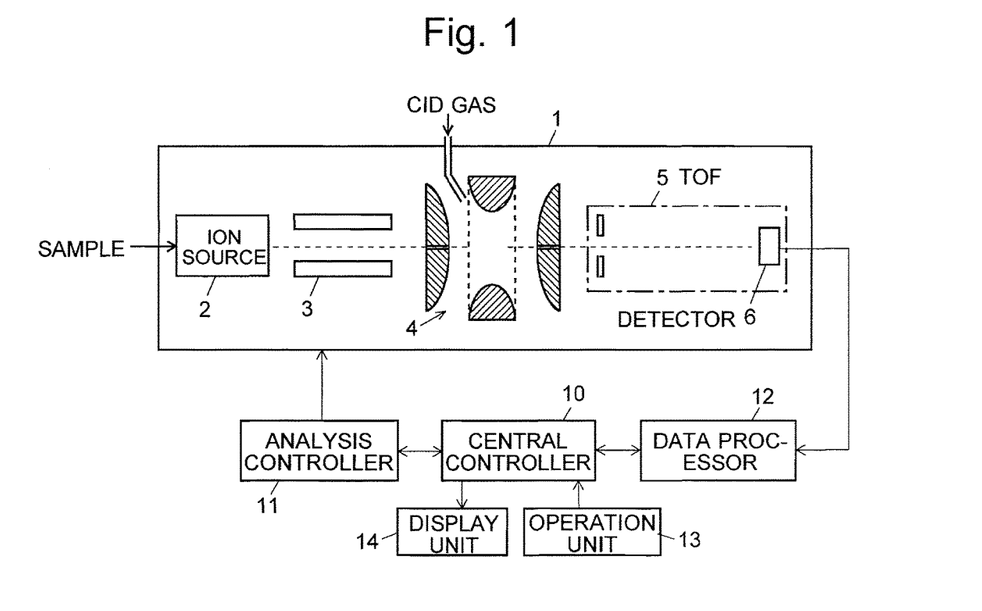
FIG. 1 is an overall configuration diagram of one embodiment of the mass spectrometer according to the present invention.

One embodiment of a mass spectrometer according to the present invention is hereinafter described with reference to the drawings. FIG. 1 is an overall configuration diagram of the present mass spectrometer.

A mass analyzer unit 1 includes an ion source 2 for ionizing sample molecules, a three-dimensional quadrupole ion trap 4 for temporarily storing ions within its internal space and for promoting collision-induced dissociation of these ions, an ion optical system 3 for guiding the ions produced by the ion source 2 to the ion trap 4, a time-of-flight mass separator (TOF) 5 for separating ions emitted from the ion trap 4 according to their mass (or mass-to-charge ratio, m/z, to be exact) and a detector 6 for detecting the ions separated by the TOF 5.

An analysis controller 11 conducts an $MS^n$ analysis by controlling the operation of each component of the mass analyzer unit 1 according to the instructions from a central controller 10. A data processor 12 receives detection signals from the detector 6, converts them into digital data and performs a predetermined data processing inclusive of a precursor-ion selection process which will be described later. An operation unit 13 and display unit 14, which constitute a user interface, are connected to the central controller 10. Most of the functions of the central controller 10, analysis controller 11 and data processor 12 can be embodied by a personal computer with a controlling and processing software program installed therein.

The basic operation of the mass spectrometer having the previously described configuration is hereinafter schematically described. When an $MS^1$ analysis, i.e. a normal mass analysis with no dissociation operation, is to be performed, the system operates as follows under the control of the analysis controller 11: The ion source 2 ionizes sample molecules to produce various kinds of ions. These ions are then introduced through the ion optical system 3 into the ion trap 4. Within the ion trap 4, the ions are temporarily captured by a quadrupole electric field formed by a radio-frequency voltage applied from a power source (not shown) to the electrodes. Subsequently, at a specific timing, kinetic energy is simultaneously given to all the ions captured in the ion trap 4, whereby the ions are ejected from the ion trap 4 and introduced into the TOF 5. This means that the ion trap 4 corresponds to the start point where the ions begin their flight to the TOF 5. While flying through the flight space inside the TOF 5, the ions are temporally separated according to their mass. The separated ions sequentially arrive at, and are detected by, the detector 6.

The data processor 12 receives this detection signal and converts the time of flight within the TOF 5 to the mass to create a mass spectrum with the horizontal axis indicating the mass and the vertical axis indicating the relative intensity. This mass spectrum is displayed via the central controller 10 on the screen of the display unit 14. Based on this mass-analysis result, the analysis operator designates one ion as a precursor ion for an MS² (MS/MS) analysis including one stage of the dissociation operation.

When the analysis operator enters, for example, the mass of the precursor ion through the operation unit 13 and gives a command to carry out the MS² analysis, the system operates as follows under the control of the analysis controller 11: The ion source 2 ionizes sample molecules to produce various kinds of ions. These ions are then introduced through the ion optical system 3 into the ion trap 4. Within the ion trap 4, the ions are temporarily captured by the aforementioned quadrupole electric field, immediately after which a voltage for dissipating unwanted ions other than the previously selected precursor ion is applied to the electrodes. As a result, only the precursor ion is left within the ion trap 4 (the selection of the precursor ion). Additionally, a CID gas is introduced from an external source. The precursor ion is dissociated due to the collision with the CID gas, whereby various kinds of product ions are produced according to the mode of dissociation.

The product ions produced by the dissociation (and the residual precursor ion, if it remains) are collectively ejected from the ion trap 4 at a predetermined timing and introduced into the TOF 5. As in the case of the normal mass analysis, the ions are temporally separated according to their mass while flying within the flight space of the TOF 5, and the separated ions sequentially arrive at, and are detected by, the detector 6. The data processor 12 receives this detection signal and converts the flight time within the TOF 5 to the mass to create an MS² spectrum. This MS² spectrum is displayed via the central controller 10 on the screen of the display unit 14.

It is also possible to perform an MS$^n$ analysis with n=3 or a greater number by repeating the dissociation operation in stages, where one of the product ions produced within the ion trap 4 in one stage of the dissociation process is chosen as a new precursor ion to be dissociated by the CID process. Although there is no theoretical limit on the number of stages of the dissociation operation, the maximum value of n is practically within the range from 3 to 6.

In the mass spectrometer of the present embodiment, the data processor 12 that has received the detection signal obtained by the MS² analysis in the previously described manner selects a precursor ion for an MS³ analysis where the number of dissociation operation is further increased by one, and the selection information of the precursor ion is sent via the central controller 10 to the analysis controller 11, which then controls the mass analyzer unit 1 so as to perform an MS³ analysis in which the selected precursor ion is used as the precursor ion in the second stage of the dissociation operation. The steps of these operations are hereinafter described with reference to FIGS. 2 to 6.

Figure 2:
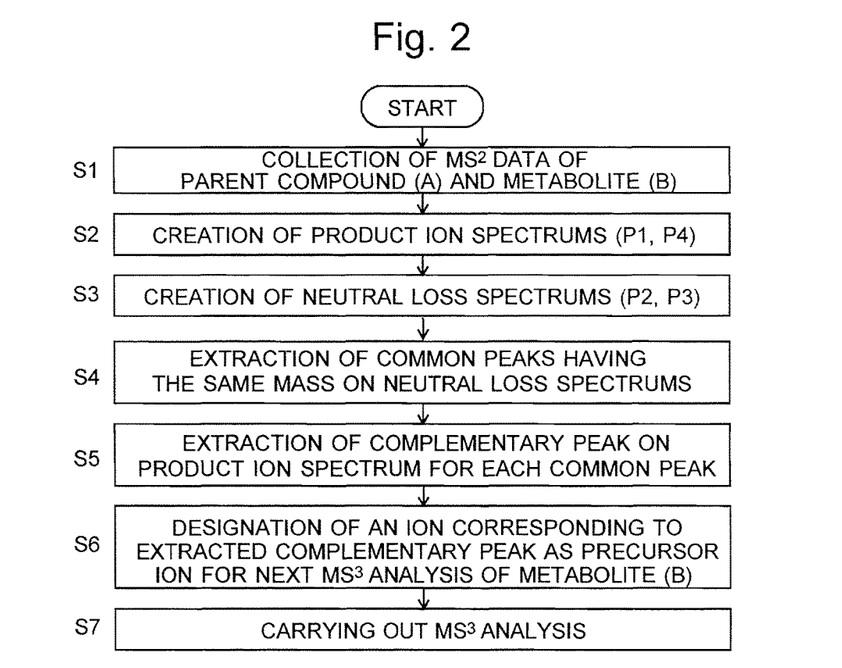
FIG. 2 is a flowchart showing one example of the analysis control operation in the mass spectrometer of the present embodiment.

As one example, the following description deals with the case of the structural analysis of a metabolite (labeled "B") originating from a parent compound (labeled "A") having a known chemical structure. FIG. 2 is a flowchart showing the control and process steps characteristic of the mass spectrometer of the present embodiment.

Figure 3:
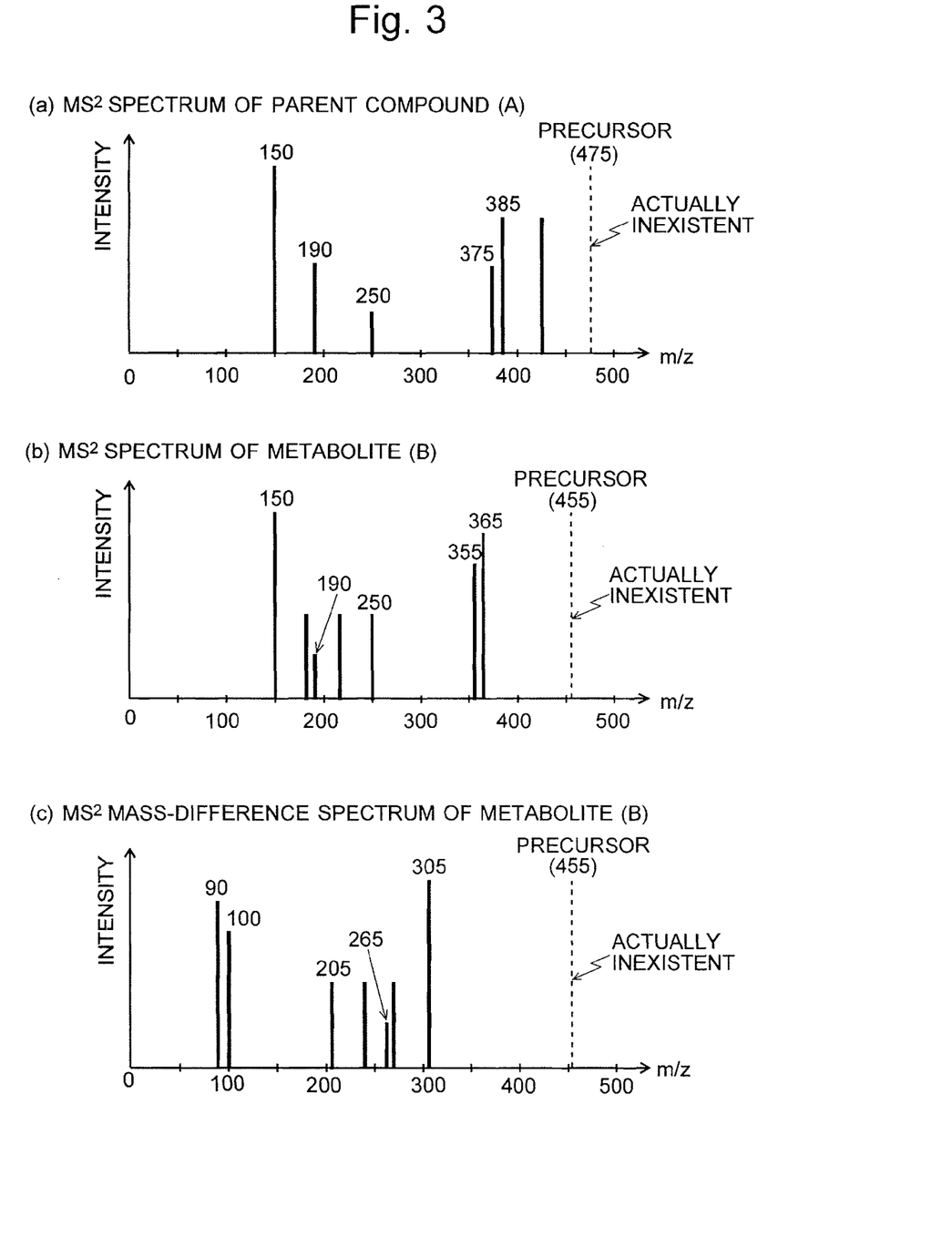
FIG. 3 is a diagram showing one example of two $MS^n$ spectrums obtained by the mass spectrometer of the present embodiment.

First, with the mass spectrometer shown in FIG. 1, an MS² analysis is respectively performed on both the parent compound (A) and metabolite (B) to collect MS² spectrum data for these compounds (Step S1). In the present example, the mass of the precursor ion used in the MS² analysis for the parent compound (A) is 475, and that of the precursor ion in the MS² analysis for the metabolite (B) is 455. FIG. 3 shows examples of the MS² spectrum of the parent compound (A) and that of the metabolite (B). Although the peak corresponding to the precursor ion in each spectrum does not actually exist, the figure shows this peak by a dotted line for easier understanding of the following description. The MS² spectrums shown in FIG. 3 illustrate the intensity of the product ions and hence are hereinafter referred to as the "product ion spectrums."

After the data have been collected in the previously described manner, when the data processing is initiated, the data processor 12 creates a product ion spectrum, as shown in FIG. 3, based on each set of the collected data (Step S2). In this step, a peak list, which relates each mass to an intensity, is created. This peak list can be graphically represented to obtain the product ion spectrum, in which the listed peaks are drawn on a graph with the horizontal axis indicating the mass and the vertical axis indicating the intensity.

Next, for the parent compound (A) and the metabolite (B), respectively, the mass difference between the mass of the precursor ion and the mass of each product ion appearing on the product ion spectrum (i.e. listed in the aforementioned peak list) is sequentially calculated for each product ion. Then, a mass-difference peak list, which relates each mass difference to the intensity of the product ion that has been the origin of the mass difference, is created. For example, in the case of FIG. 3(*a*) where the mass of the precursor ion is 475, a product ion having a mass of 150 has a mass difference of 325, and this mass difference is related to the intensity of the peak of the product ion having a mass of 150 and registered in the mass-difference peak list. This operation is similarly performed for each and every peak appearing on the product ion spectrum to complete a mass-difference peak list. A graphical representation of this peak list is the aforementioned MS² mass-difference spectrum, in which the listed peaks are drawn on a graph with the horizontal axis indicating the mass and the vertical axis indicating the intensity. The MS² mass-difference spectrum created from the MS² spectrum in FIG. 3(*b*) is shown in FIG. 3(*c*). The mass difference corresponds to the mass of a fragment desorbed from the precursor ion due to the dissociation. On the assumption that the precursor ion is monovalent, the desorbed fragment is a neutral molecule. Accordingly, the MS² mass-difference spectrum is hereinafter called the "neutral loss spectrum" (Step S3).

By the processes in Steps S2 and S3, the product ion spectrum and neutral loss spectrum relating to the parent compound (A) and those spectrums relating to the metabolite (B) are created. Subsequently, the mass-difference peak list of the parent compound (A) and that of the metabolite (B) are compared to locate a peak having the same mass and extract this peak as a common peak on the neutral loss spectrum (Step S4).

Figure 4:
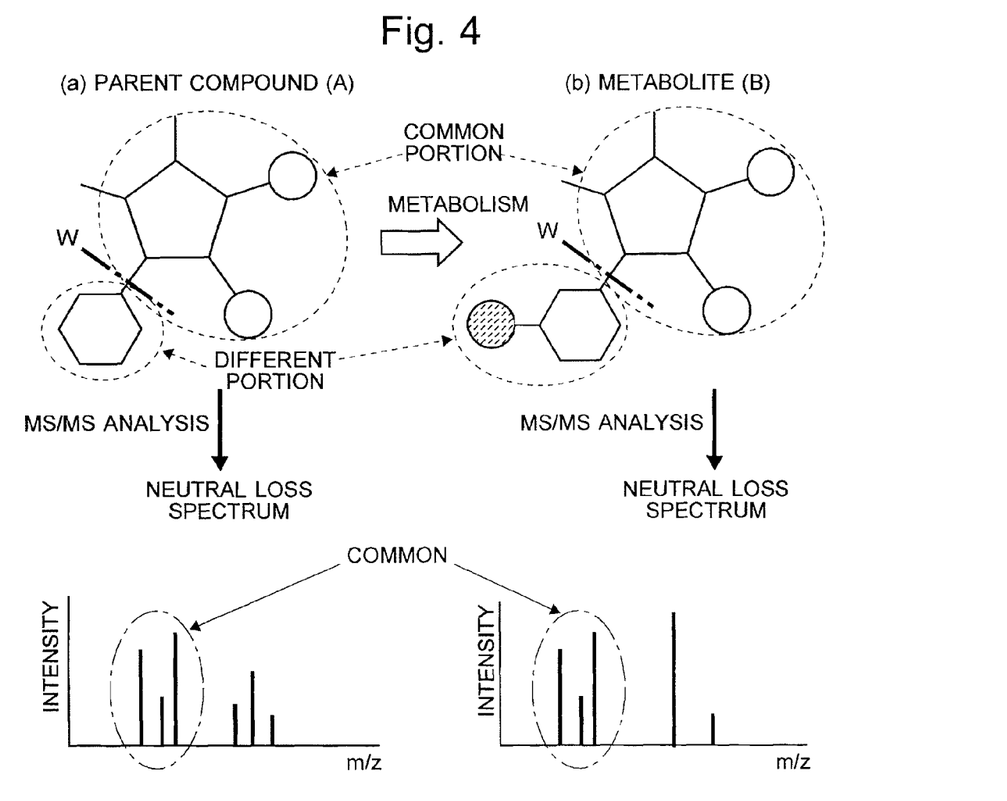
FIG. 4 is a diagram for explaining the analysis control operation in the mass spectrometer of the present embodiment.

The meaning of the common peak on the neutral loss spectrum is hereinafter explained by FIG. 4. It is assumed that a parent compound (A) having a chemical structure schematically shown in FIG. 4(*a*) has its structure partially modified by a metabolic process and turned to a metabolite (B) having a chemical structure shown in FIG. 4(*b*). If, as a result of a dissociation operation in an MS² analysis, both the parent compound (A) and the metabolite (B) have been split at the section W in the figures, one of the resultant fragments will be a common portion having the same structure and the other one will be a different portion modified by the metabolic process. If the dissociation operation causes the different portion to remain in the form of an ion and the common portion to be desorbed in the form of a neutral molecule, the common portion will appear as a common peak on the neutral loss spectrums of the parent compound (A) and the metabolite (B). As already stated, the product ion has resulted from the desorption of the neutral molecule from the original precursor ion. Therefore, subtracting the mass corresponding to the common peak from the mass of the precursor ion should come to the mass of the different portion.

Next, for each of one or more common peaks appearing on the neutral loss spectrum of the metabolite (B), the mass of a complementary peak to be paired with the common peak in question is calculated. The phrase "to be paired" means that the total of the masses of the common peak and complementary peak should equal the mass of the precursor ion. The mass of the complementary peak to be paired with a given common peak can be obtained by subtracting the mass of the common peak from that of the precursor ion. For example, the peak with a mass of 90 in FIG. 3(c) is a common peak on the neutral loss spectrum and should have the complementary peak located at a mass of 365 on the product ion spectrum since subtracting 90 from 455 (i.e. the mass of the precursor ion) comes to 365. After the masses of the complementary peaks corresponding to all the common peaks on the neutral loss spectrum have been thus calculated, these complementary peaks are extracted from the peak list (Step S5).

Figure 5:
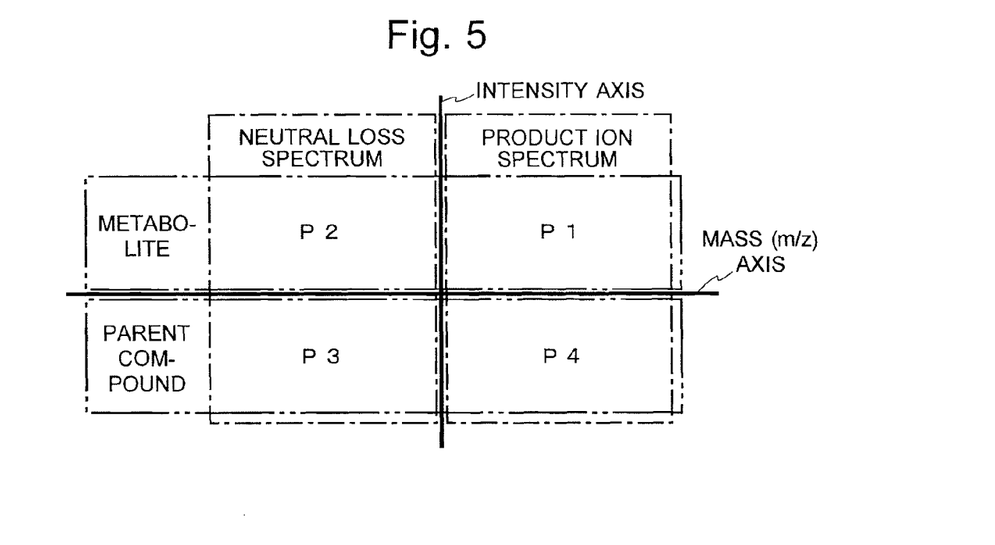
FIG. 5 is a model diagram for explaining the method of displaying spectrums by the mass spectrometer of the present embodiment.

The four spectrums (product ion spectrums and neutral loss spectrums) created in Steps S2 and S3 may be preferably shown on the same display screen of the display unit 14. One example is shown in FIG. 5, where the product ion spectrum P1 of the metabolite (B) and the product ion spectrum P4 of the parent compound (A) are symmetrically arranged with respect to the horizontal mass axis, and the neutral loss spectrum P2 of the metabolite (B) and the neutral loss spectrum P4 of the parent compound (A) are also symmetrically arranged with respect to the same horizontal mass axis, with each neighboring pair of the product ion spectrum and neutral loss spectrum being symmetrically arranged with respect to the vertical intensity axis.

Figure 6:
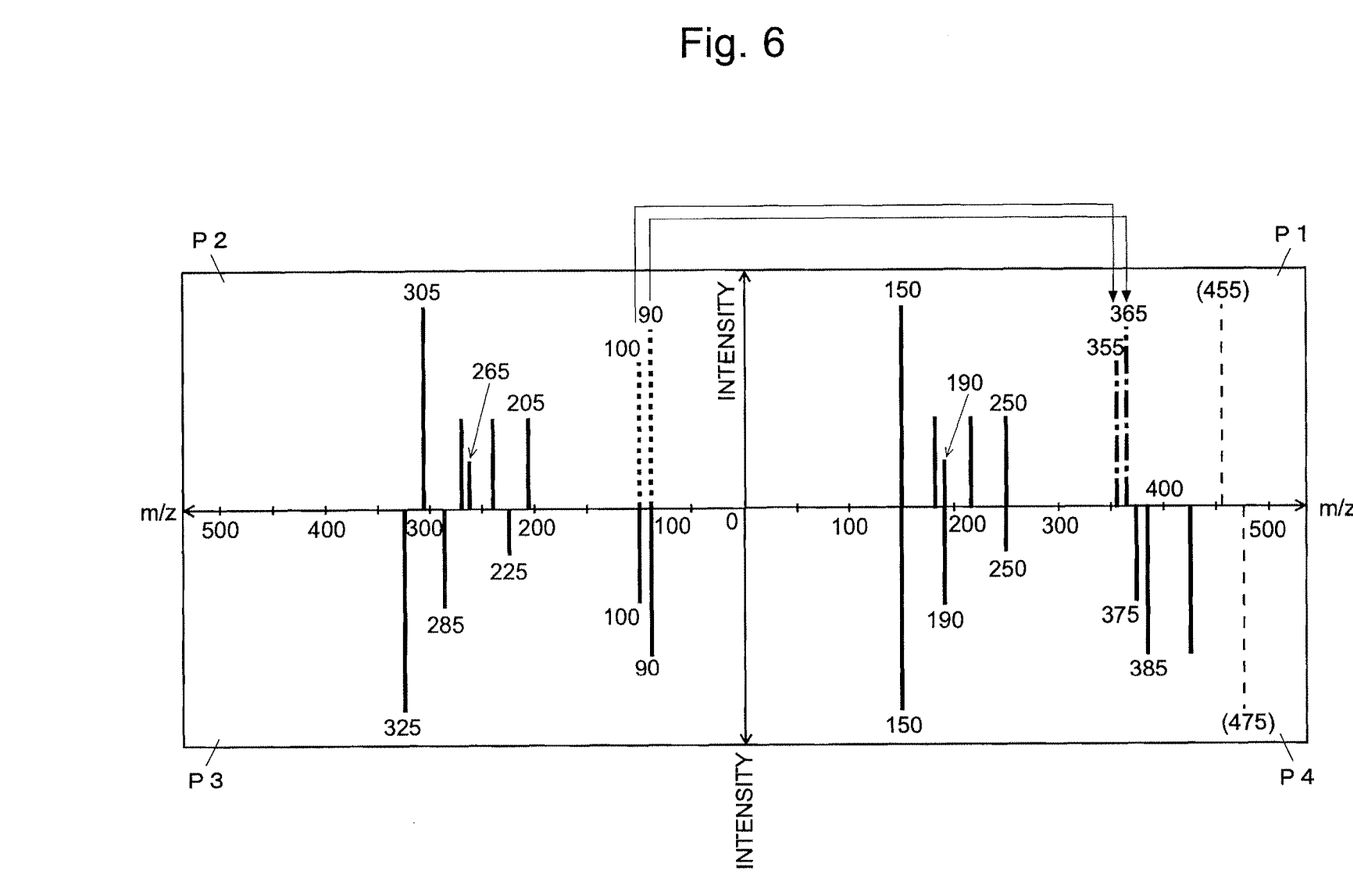
FIG. 6 is a chart for explaining the method of displaying $MS^n$ spectrums by the mass spectrometer of the present embodiment.

FIG. 6 is an example of the display format for integrating the product ion spectrums of the parent compound (A) and the metabolite (B) shown in FIG. 3 as well as the neutral loss spectrums derived from those product ion spectrums. In this example, each common peak is represented by a pair of lines that respectively extend upwards and downwards from the mass axis. In order to highlight the common peaks in the neutral loss spectrum of the metabolite (B), the display color for the common peaks are set so that they are drawn in a color different from the color of the other peaks. Furthermore, in order to highlight the complementary peaks in the product ion spectrum of the metabolite (B), the display color for the complementary peaks are also set so that they are drawn in a color different from the color of the other peaks. It should be noted that, since the difference in color cannot be actually represented in FIG. 6, dotted lines are used to identify the common peaks to be drawn in a different color and chained lines are used to identify the complementary peaks to be drawn in a different color. For example, the common peaks may be drawn in red, the complementary peaks in blue, and the other peaks in black. The arrowed lines in FIG. 6, which show the relationships between the common peaks and the complementary peaks, may or may not be actually drawn on the display screen.

In the present example, the product ion spectrum has two complementary peaks at masses of 355 and 365, respectively. As already explained, it is highly probable that an ion having the mass of a complementary peak corresponds to the different portion, or the site of metabolism, of the metabolite (B). Therefore, the data processor 12 sends mass information of the complementary peak to the analysis controller 11.

According to this information, the analysis controller 11 designates this mass as a precursor ion for the second stage of the dissociation operation in the $MS^3$ analysis for the metabolite (B) (Step S6). It should be noted that the precursor ion in the first stage of the dissociation operation in the $MS^3$ analysis is the ion having a mass of 455, which is the same as used in the $MS^2$ analysis. Upon receiving a command to carry out the $MS^3$ analysis for the metabolite (B), the analysis controller 11 collects $MS^3$ analysis data by performing a dissociation operation on the precursor ion selected in the previously described manner (Step S7).

As just described, the mass spectrometer of the present embodiment automatically designates an ion corresponding to the site of metabolism characteristic of the metabolite (B) as a precursor ion, and then performs an $MS^3$ analysis. Instead of automatically designating an ion corresponding to a complementary peak as a precursor ion, it is possible to give the ion a higher degree of priority as a candidate of the precursor ion and sequentially perform $MS^n$ analyses of the candidate ions in the order of priority when the $MS^n$ analysis of the metabolite (B) is carried out. In this case, it is also possible to provide a function for allowing an analysis operator to intentionally lower the priority of any candidate ion and thereby exclude this ion from the $MS^3$ analysis due to a personal judgment or other criteria even if the ion has been given a high degree of priority in the aforementioned precursor-ion selection process.

The previous embodiment assumed that the structurally different portions of the parent compound (A) and the metabolite (B) appeared on the neutral loss spectrums as a result of an $MS^2$ analysis. However, the method of the previous embodiment cannot be applied to the case where the different portions are desorbed in the form of neutral molecules and the common portion remains in the form of an ion. In such a case, a technique similar to Step S4 can be used, in which a common peak is extracted from the product ion spectrums and the ion corresponding to this common peak is excluded from the candidates of the precursor ion in the $MS^3$ analysis or ranked at a low priority level, based on the judgment that the ion corresponding to the aforementioned common peak is not characteristic of the site of metabolism of the metabolite (B). By this technique, the ions that do not provide useful information can be excluded when the precursor ion for the $MS^3$ analysis is to be selected from the product ion spectrums. This will facilitate the narrowing down of the candidates of the precursor ion and consequently improve the efficiency of the structural analysis.

In the previous embodiment, the precursor-ion selection process was performed using the result obtained by an $MS^n$ analysis. It is naturally possible to apply the same process to a result obtained by an $MS^3$ analysis, $MS^4$ analysis or other modes of $MS^n$ analysis with n set to any values greater than one.

Furthermore, any changes, modifications or additions appropriately made within the spirit of the present invention in any other aspects of the system will also naturally fall within the scope of claims of this patent application.

The invention claimed is:

1. A mass spectrometer, comprising:
a mass analyzer unit that provides an $MS^n$ analysis (where n is an integer greater than two), the mass analyzer unit including an ion source and a detector, and the mass analyzer unit performing $MS^{m-1}$ analysis (where m is an integer greater than two and no greater than n) on a first component and a second component to obtain mass analysis data for the first component and mass analysis data for the second component from the detector and performing an $MS^m$ analysis including a dissociation operation on the first component and/or the second component;

a controller configured to control the dissociation operation; and a data processor configured for
- a) creating an $MS^{m-1}$ spectrum (where m is an integer greater than two and no greater than n) based on the mass analysis data for the first component, and creating an $MS^{m-1}$ spectrum based on the mass analysis data for the second component;
- b) extracting a common peak having a same mass to charge ratio in the two $MS^{m-1}$ spectrums relating to the first component and the second component;
- c) either excluding an ion corresponding to the common peak, or giving a low degree of priority to this ion, as a candidate of a precursor ion for an m-1-th stage of the dissociation operation in the $MS^m$ analysis on the first component and/or the second component;
- d) designating an ion corresponding to a complementary peak as the precursor ion for the m-1-th stage of the dissociation operation in the $MS^m$ analysis on the first component and/or the second component while excluding or giving a low degree of priority to the ion corresponding to the common peak; and
- e) acquiring a subsequent $MS^m$ spectrum from the dissociation operation.

2. A method of providing an $MS^n$ analysis (where n is an integer greater than two), comprising:
- a) performing $MS^{m-1}$ analysis (where m is an integer greater than two and no greater than n) on a first component and a second component using a mass spectrometer, including an ion source and a detector, to obtain mass analysis data for the first component and mass analysis data for the second component from the detector;
- b) creating an $MS^{m-1}$ spectrum (where m is an integer greater than two and no greater than n) based on the mass analysis data obtained by the $MS^{m-1}$ analysis performed for the first component, and creating the $MS^{m-1}$ spectrum based on the mass analysis data obtained by the $MS^{m-1}$ analysis performed for the second component;
- c) extracting a common peak having a same mass to charge ratio in the two $MS^{m-1}$ spectrums relating to the first component and the second component;
- d) either excluding an ion corresponding to the common peak, or giving a low degree of priority to this ion, as a candidate of a precursor ion for an m-1-th stage of a dissociation operation in an $MS^m$ analysis on the first component and/or the second component,
- e) designating an ion corresponding to a complementary peak as the precursor ion for the M-1-th stage of the dissociation operation in the MSm analysis on the first component and/or the second component while excluding or giving a low degree of priority to the ion corresponding to the common peak;
- f) performing the $MS^m$ analysis including a dissociation operation on the first component and/or the second component using the mass spectrometer; and
- g) acquiring a subsequent $MS^m$ spectrum from the dissociation operation.

* * * * *